United States Patent [19]

Gurtler et al.

[11] Patent Number: 5,279,962
[45] Date of Patent: Jan. 18, 1994

[54] **MUTANTS OR VARIANTS OF *BACILLUS THURINGIENSIS* PRODUCING HIGH YIELDS OF DELTA ENDOTOXIN**

[75] Inventors: Hanne Gurtler, Holte; Annette S. Petersen, Birkerod, both of Denmark

[73] Assignee: Novo Nordisk A/S, Bagsvaerd, Denmark

[21] Appl. No.: 906,038

[22] Filed: Jun. 26, 1992

Related U.S. Application Data

[63] Continuation of Ser. No. 613,337, Nov. 14, 1990, abandoned.

[30] Foreign Application Priority Data

Nov. 17, 1989 [DK] Denmark ............................ 5805/89
Dec. 12, 1989 [DK] Denmark ............................ 6274/89

[51] Int. Cl.$^5$ ..................... C12N 1/20; C12N 1/00; A01N 63/00
[52] U.S. Cl. ................... 435/252.5; 435/832; 424/93 L
[58] Field of Search ............... 435/252.31, 252.5, 832; 424/93

[56] References Cited

U.S. PATENT DOCUMENTS

| | | |
|---|---|---|
| 4,277,564 | 7/1981 | Johnson . |
| 4,764,372 | 8/1988 | Herrnstadt et al. .................... 424/93 |
| 4,766,203 | 8/1988 | Krieg et al. ............................ 424/93 |
| 4,797,279 | 1/1989 | Karamata et al. ..................... 424/93 |
| 4,910,016 | 3/1990 | Gaertner et al. ................. 435/252.5 |
| 4,966,765 | 10/1990 | Payne et al. ...................... 435/252.5 |
| 4,990,332 | 2/1991 | Payne et al. ............................ 424/93 |
| 4,996,156 | 2/1991 | Zaehner et al. ................... 435/252.5 |
| 4,999,192 | 3/1991 | Payne et al. ...................... 435/252.5 |
| 5,006,336 | 4/1991 | Payne et al. ...................... 435/252.5 |

FOREIGN PATENT DOCUMENTS

| | | |
|---|---|---|
| 0099301 | 7/1982 | European Pat. Off. . |
| 0228228 | 7/1987 | European Pat. Off. . |
| 0278035 | 8/1988 | European Pat. Off. . |
| 0325037 | 7/1989 | European Pat. Off. . |
| 0328383 | 8/1989 | European Pat. Off. . |
| 0330342 | 8/1989 | European Pat. Off. . |
| 0366398 | 5/1990 | European Pat. Off. . |

OTHER PUBLICATIONS

Wakisaka et al., App. Env. Microbiol., vol. 43, No. 6, pp. 1498-1500 (1982).
Dulmage et al., J. Invert. Path., vol. 22, pp. 273-277 (1974).
Krieg et al., Sys. Appl. Microbiol., vol. 9, pp. 138-141 (1987).
Herrnstadt et al., Bio/Technology, vol. 4, pp. 305-308 (1986).
Huger et al., J. Appl. Ent., vol. 108, pp. 490-497 (1989).
Krieg et al., J. Appl. Ent., vol. 104, 417-424 (1987).
de Barjac et al., Entomophaga, vol. 35, No. 2, pp. 233-240 (1990).
Johnson et al., Appl. Env. Microbiol., vol. 42, No. 2, pp. 385-387 (1981).
Payne et al., 1984 British Crop Protect. Conf.-Pests and Diseases, pp. 231-238 (1984).
Krieg et al., J. App. Ent., vol. 96, pp. 500-508 (1983).
Nishiitsutsuji-Uwo et al., J. Invert. Path., vol. 25, pp. 355-361 (1975).
Dulmage et al., Chem. Abs., vol. 80, No. 3, p. 323, abstract No. 13629p (1974).
Johnson et al, Appl. & Environ. Microbiol., 42 (2), Aug. 1981, pp. 385-387.
C. C. Payne et al, British Crop Protection Conference--Pests & Diseases, 1984, pp. 231-238.

*Primary Examiner*—Douglas W. Robinson
*Assistant Examiner*—Susan M. Dadio
*Attorney, Agent, or Firm*—Steve T. Zelson; Cheryl H. Agris

[57] ABSTRACT

This invention relates to mutants or variants of *Bacillus thuringiensis* producing high amounts of active delta-endotoxins. The delta-endotoxins produced by the mutant or variant B. thuringiensis will have an activity directed towards the same pest insects as its parent *B. thuringiensis* delta-endotoxins, such as against lepidopterans (mutants from B. thuringiensis subsp. kurstaki or subsp. *aizawai*), dipterans (mutants from *B. thuringiensis* subsp. *israelensis*) or coleopterans (mutants from *B. thuringiensis* subsp. *tenebrionis*).

1 Claim, No Drawings

MUTANTS OR VARIANTS OF *BACILLUS THURINGIENSIS* PRODUCING HIGH YIELDS OF DELTA ENDOTOXIN

This application is a continuation application of copending application Ser. No. 07/613,337, filed Nov. 14, 1990, now abandoned.

BACKGROUND OF THE INVENTION

Commercial preparations of *Bacillus thuringiensis* are used worldwide for biological control of pest insects. The advantages of these bacterial insecticides are that they are highly selective for a very limited range of target insects and are biodegradable.

Commercial preparations of *Bacillus thuringiensis* can be applied right up to the time of harvest with no adverse effects.

*Bacillus thuringiensis* is a rodshaped, aerobic, spore forming bacterium uniquely characterized by the production during the sporulation process of one or more inclusions, referred to as parasporal crystals. These crystals are composed of high molecular weight proteins, referred to as delta-endotoxins. The delta-endotoxins are the active ingredient in available commercial preparations of *Bacillus thuringiensis*.

Many *B. thuringiensis* strains with different insect host spectra have been identified. They are classified into different subspecies based on their flagellar antigens. Of particular interest is *Bacillus thuringiensis subspecies kurstaki* and *subspecies aizawai* used for the control of lepidopteran pest insects, *Bacillus thuringiensis subspecies israelensis* used for the control of dipteran pest insects and *Bacillus thuringiensis subspecies tenebrionis* used for the control of coleopteran pest insects.

The first isolation of a coleopteran toxic *Bacillus thuringiensis* was reported in 1983 (A. Krieg et al., Z.and.Ent. 96, 500–508, European Patent Publication EP 0149162 A2).

The isolate, which was designated *Bacillus thuringiensis subsp. tenebrionis*, has been deposited with the German Collection of Microorganisms under accession number DSM 2803. *Bacillus thuringiensis subsp. tenebrionis* was isolated in 1982 from a dead pupa of the mealworm, *Tenebrio molitor* (*Tenebrionidae, Coleoptera*). The strain produces within each cell one spore and one or more insecticidal parasporal crystals which are of flat platelike form with an edge length of about 0.8 μm to 1.5 μm. It belongs to serotype H8a,8b and pathotype C of *Bacillus thuringiensis* (Krieg et al., System.Appl.Microbiol. 9, 138–141, 1987, U.S. Pat. No. 4,766,203, 1988).

It is only toxic against certain leaf eating beetle larvae (*Chrysomelidae*), but ineffective against caterpillars (Lepidoptera), mosquitoes (Diptera) or other insects.

*Bacillus thuringiensis subsp. tenebrionis* has been shown to be an effective control agent for the colorado potato beetle larvae. After uptake of crystals and spores from *Bacillus thuringiensis subsp. tenebrionis* or isolated crystals larvae, and to a certain extent adults, of the colorado potato beetle (*Leotinotarsa decemlineata*) stop feeding. Larval stages L1-L3 die within 1-3 days (Schnetter et al., in "Fundamental & applied aspects of invertebrate pathology", eds. R.A. Samson et al., Proceedings of the 4th Int. colloquium of Invertebrate Pathology, p. 555, 1986).

It has recently been shown that *Bacillus thuringiensis subsp. tenebrionis* in addition to the coleopteran active crystal also produces another parasporal crystal that is spindle-, speroidal or plateshaped (A.M. Huger & A. Krieg, J.Appl.Ent. 108, 490–497, 1989). The activity of the second crystal is not yet known.

Four commercial products of *Bacillus thuringiensis subsp. tenebrionis* have been developed for the control of coleopteran pests. NOVODOR ® from Novo Nordisk A/S, TRIDENT ® from Sandoz, and DiTerra ® from Abbott Laboratories Inc., and Foil ® from Ecogen.

The isolation of another coleopteran toxic *Bacillus thuringiensis* strain was reported in 1986 (Hernnstadt et al. Bio/Technology vol. 4, 305–308, 1986, U.S. Pat. No. 4,764,372, 1988). This strain, designated "*Bacillus thuringiensis subsp. san diego*", M7, has been deposited at the Northern Regional Research Laboratory, USA under accession number NRRL B-15939. A commercial product based on "*Bacillus thuringiensis subsp. san diego*" has been developed by Mycogen Corp.

Comparative studies of *Bacillus thuringiensis subsp. tenebrionis*, DSM 2803 and "*Bacillus thuringiensis subsp. san diego*", NRRL-B 15939 including phenotypic characterization of the vegetative cells, characterization of the toxic parasporal crystal and analysis of plasmid DNA have, however, shown that "*Bacillus thuringiensis subsp. san diego*" apparently is identical to the formerly isolated strain DSM 2803, *Bacillus thuringiensis subsp. tenebrionis* (Krieg et al.: J.Appl.Ent. 104, 417–424, 1987). Furthermore, the nucleotide sequences and deduced amino acid sequences of the coleopteran active delta endotoxin genes from *Bacillus thuringiensis subsp. tenebrionis* and "*Bacillus thuringiensis subsp. san diego*" are identical.

Under the same culture conditions the above-mentioned second type of crystals are also synthesized by "Bacillus thuringiensis subsp. san diego" (A.M. Huger & A. Krieg, J.Appl.Ent. 108, 490–497, 1989).

According to H. de Barjac & E. Frachon (Entomophaga 35(2), 233–240, 1990) the "san diego" isolate is similar to "tenebrionis" and it cannot be justified to regard it as a different subspecies.

The utility of Bacillus thuringiensis strains for the control of coleopteran pests is dependent upon efficient and economical production of the coleopteran active toxins and the potency of the product produced. This in turn is dependent upon the amount of delta endotoxins which can be produced by fermentation of the coleopteran active *Bacillus thuringiensis* strains.

B. thuringiensis has been used for many years for the production of insecticides, but although mutants of B. thuringiensis with increased delta-endotoxins yield would be advantageous, no such mutants have previously been described. Mutants producing higher yields of delta-endotoxins would give a more efficient and economical production of *B. thuringiensis* toxins and a possibility for manufacture of *B. thuringiensis* products with increased potency at equal cost. This in turn would be an advantage for the user as reduced volumes of pesticide formulation have to be stored and handled for a given acreage. In addition, the users will have less container material to dispose of, thereby reducing the impact on the environment.

Improvements of the production of delta endotoxin by *Bacillus thuringiensis subsp. tenebrionis* through mutation have not previously been reported.

One problem associated with the use of especially *B. thuringiensis subspecies tenebrionis* in controlling beetle larvae has been the relatively low potency or strength of the preparations requiring the application of relatively large amounts of preparation to the areas to be treated, such as 5 to 10 liter/ha compared to 1 to 2 liter/ha of most other *B. thuringiensis* products and most other insecticides.

Consequently a recognized need for products of improved strength exists.

One way to overcome this problem would be to concentrate the preparations. However, this would add considerably to the production cost in comparison to the savings obtained in storage and transportation.

A much more elegant solution would be to create mutants of existing *B. thuringiensis* strains capable of producing substantially larger amounts of delta endotoxins per cell.

SUMMARY OF THE INVENTION

The present invention consequently in one aspect relates to variant or mutant *Bacillus thuringiensis* strains capable of producing substantially larger amounts of toxins than their parent strain.

In another aspect the invention relates to such high producing variants or mutants of *B. thuringiensis* strains belonging to the *subspecies tenebrionis*.

Further aspects of the invention relate to the use of such variant or mutant *Bacillus thuringiensis* strains for the production of pesticidal products, and also to such pesticidal compositions comprising as the active ingredient delta-endotoxins produced by the variant or mutant *Bacillus thuringiensis* strains of the invention.

Also, the invention in one of its aspects relate to a method of controlling pests by applying a composition according to the invention to an area where pests susceptible to the activity of the delta-endotoxins in question are to be controlled.

In a still further aspect this invention relates to methods of selecting, or mutating and selecting *B. thuringiensis* strains in order to obtain such variated or mutated *B. thuringiensis* strains capable of producing substantially larger amounts of delta endotoxins than their parent strain.

DEPOSIT OF MICROORGANISMS

For the purpose of describing this invention in detail a mutant of *Bacillus thuringiensis subsp. tenebrionis* which produces high amounts of delta-endotoxin has been deposited with the Deutsche Sammlung von Mikroorganismen und Zellkulturen GmbH, Mascheroderweg 1b, D-3300 Braunschweig, Federal Republic of Germany, for the purposes of patent procedure on the date indicated below. DSM being an international depositary under the Budapest Treaty affords permanence of the deposit in accordance with rule 9 of said treaty.

| Deposit date | 10 August 1989 |
|---|---|
| Depositor's ref. | NB 176-1 |
| DSM designation | DSM 5480 |

The mutant DSM 5480 was obtained by mutation of *Bacillus thuringiensis subsp. tenebrionis*, strain DSM 5526, that has also been deposited under the Budapest Treaty as indicated below:

| Deposit date | 14 September 1989 |
|---|---|
| Depositor's ref. | NB 125 |
| DSM designation | DSM 5526 |

DETAILED DESCRIPTION OF THE INVENTION

This invention relates in its general aspect to variants or mutants of *Bacillus thuringiensis* producing high amounts of active delta-endotoxins as compared to its parent strain.

In this context the expression "high amounts" preferably means at least twice as much or more.

Both in this general aspect and the more specific aspects of the invention indicated below, the delta-endotoxins produced by a mutant *B. thuringiensis* will have an activity directed towards the same pest insects as its parent *B. thuringiensis* delta-endotoxins, such as against lepidopterans (mutants from *B. thuringiensis subsp. kurstaki* and *subsp. aizawai*), dipterans (mutants from *B. thuringiensis subsp. israelensis*) or coleopterans (mutants from *B. thuringiensis subsp. tenebrionis*).

In one specific embodiment of this aspect of the invention the *B. thuringiensis* belongs to the subspecies tenebrionis, and the delta-endotoxin produced is active against coleopterans.

Under this aspect a preferred embodiment of the invention the variated or mutated *B. thuringiensis subsp. tenbrionis* is capable of producing more than three times as much delta endotoxin as the strain DSM 2803.

Further embodiments of the invention comprise variants or mutated *B. thuringiensis subsp. tenebrionis* strains that are capable of producing a parasporal crystal having a mean edge length of 2 μm or more.

A still further embodiment of the invention oomprises varianted or mutated *B. thuringiensis subso. tenebrionis* strains showing a sporulation frequency 10 to 100 or even $10^6$ times lower than the sporulation frequency of the parent strain or the strain DSM 2803.

An even more specific embodiment comprises the deposited mutant *B. thuringiensis subsp. tenebrionis* DSM 5480.

While working on this invention a mutant of *B. thuringiensis subsp. tenebrionis* (DSM 5480) with more than a twofold increase in delta-endotoxin production as compared to its parent strain (DSM 5526) has been isolated. Phase contrast microscopy, scanning electron microscopy and transmission electron microscopy of this mutant indicate that the high productivity of this mutant is due to changes in the regulation of delta endotoxin production relative to sporulation resulting in the production of protein crystals which are up to more than five times bigger than the crystals produced by the existing coleopteran active *Bacillus thuringiensis* strains. The close correlation between crystal formation and sporulation seems to have been removed and the mutant produces high amounts of delta endotoxin prior to sporulation.

In one of its aspects the invention relates to the use of the variated or mutated strains of the invention in a method for the production of insecticidal *B. thuringiensis* products, by which method the variant or mutant *B. thuringiensis* strain is cultivated in a suitable culture medium comprising sources for carbon, nitrogen, and other components known to the skilled person for a suitable period of time, whereafter the delta endotoxins are recovered.

In a further aspect of the invention the *B. thuringiensis* delta endotoxins product obtained as above is used in pesticidal compositions as an active component.

In such compositions the delta endotoxins of the invention may be utilized either alone or in combination with other biocidally active products.

The invention also relates to such pesticidal compositions or preparations comprising the *B. thuringiensis* delta endotoxin product of the invention in admixture with agriculturally acceptable diluents or carriers.

The invention also relates to such pesticidal compositions or preparations comprising a *B. thuringiensis* delta endotoxin product, which pesticidal composition in a liquid form has a potency of at least 15,000 BTTU/g, corresponding to at least 3% w/w coleopteran insecticidal crystal protein, or which pesticidal composition in a dry form has a potency of at least 50,000 BTTU/g, corresponding to at least 10% w/w coleopteran insecticidal crystal protein.

In a specific embodiment the invention relates to pesticidal compositions produced from DSM 5480 having at least twice the potency of pesticidal compositions produced from DSM 2803 or other coleopteran active Btt strains.

The compositions of the invention can take any form known in the art for the formulation of agrochemicals, for example, a suspension, a dispersion, an aqueous emulsion, a dusting powder, a dispersible powder, an emulsifiable concentrate or granules. Moreover it can be in a suitable form for direct application or as a concentrate or primary composition which requires dilution with a suitable quantity of water or other diluent before application.

The concentration of the insecticidally active *B. thuringiensis* delta endotoxins in the compositions of the present invention when used alone or in combination with another pesticide, as applied to plants is preferably within the range from about 0.5 to about 25 per cent by weight, especially 1 to 15 per cent by weight.

In a still further aspect the invention relates to a method of controlling pests, wherein a pesticidal composition according to the preceding aspect is applied to an area infected with said pest.

In a specific embodiment the pest to be controlled belongs to the group comprising lepidopterans, dipterans, and coleopterans, especially a coleopteran, such as the colorado potato beetle.

In specific embodiments the pest can be controlled by the application of 1 quart per acre of a liquid pesticidal composition, or by the application of 0.5 lb. per acre of a dry pesticidal composition.

The active *B. thuringiensis* preparation or the compositions of the invention can be applied directly to the plant by, for example, spraying or dusting at the time when the pest has begun to appear on the plant. The preferred mode of application is by spraying. It is generally important to obtain good control of pests in the early stages of larval development as this is the time when the plant has suffered least damage.

In one method of mutating *Bacillus thuringiensis* strains and selecting such mutants that are capable of producing substantially larger amounts of delta endotoxins than their parent strains, the parent strain is:
i) treated with a mutagen,
ii) the thus treated mutants are grown on a medium suitable for the selection of asporogenous and/or oligosporogenous strains,
iii) translucent colonies are selected and grown in a medium that does not fluidize on heating, and
iv) truly asporogenous strains are deselected by subjecting the colonies to a heat treatment.

According to a preferred embodiment of this method the thus selected colonies are grown in a normal production medium, and a final selection for strains capable of increasing the delta endotoxin production is performed.

In step (i) of the above method the mutagen may be any suitable conventional chemical mutagen, such as N-methyl-N'-nitro-N-nitrosoguanidine, or ethyl methanesulfonate, or the parent strain may be treated with electromagnetic radiation, such as $\gamma$-, X-ray-, or UV-radiation.

In step (ii) a suitable medium could be a modified nutrient sporulation medium including phosphate (NSMP medium) as described by Johnson et al., In "Spores VI": eds. P. Gerhardt et al., pp. 248-254, 1975.

In step (iv) of the method of the invention a suitable medium could be a NSMP medium supplemented with $MgCl_2$ and Gelrite, Kelco.

Another method of obtaining the high producing variants or mutants of the invention may be contemplated such as growing the parent strain in a liquid medium and selecting spontaneous mutants or variants after spreading the culture broth on an agar medium suitable for selection of asporogeneous and/or oligosporogenous mutants.

Other methods of screening for the high producing variants or mutants of the invention may be contemplated such as using the mass of these mutants directly through centrifugation or other means of separating for mass.

EXAMPLE 1

A mutant of *B. thuringiensis* subsp. *tenebrionis* with more than a twofold increase in delta-endotoxin production has been isolated. Phase contrast microscopy, scanning electron microscopy and transmission electron microscopy of this mutant indicate that the high productivity of this mutant is due to changes in the regulation of delta endotoxin production relative to sporulation resulting in the production of protein crystals which are up to more than five times bigger than the crystals produced by the existing coleopteran active *Bacillus thuringiensis* strains. The close correlation between crystal formation and sporulation seems to have been removed and the mutant produces high amounts of delta-endotoxin prior to sporulation.

Production of High Yield Mutant

Spores of *B. thuringiensis* subsp. *tenebrionis*, strain DSM5526 were $\gamma$-irradiated to give a dosis of 7 kGy. The irradiated spores were spread onto NSMP agar plates (modified nutrient sporulation medium including phosphate as described by Johnson et al., In "Spores VI": eds. P. Gerhardt et al., pp. 248-254, 1975). A medium suitable for selection of asporogenous and/or oligosporogenous mutants.

The NSMP-agar plates were incubated at 30° C. for 2-3 days. Translucent colonies were picked out and transferred to NSMP gelrite plates (NSMP medium supplemented with $MgCl_2$ (0.57 g/l) and gelrite, Kelco (20 g/l)).

The NSMP gelrite plates were incubated for one hour and then further incubated for 1-2 days at 30° C. at 90° C.

Mutants that grew well on the NSMP gelrite plates were selected. In this way all asporogenous mutants were deselected as they fail to grow after the heat treatment.

The selected mutants were grown in shakeflasks containing a commercial medium. The amounts of delta-endotoxin produced were determined by immunological methods described below.

Only mutants producing significantly higher amounts of delta-endotoxin than the parent strain were selected.

The morphology of the selected mutants on solid medium and in liquid media were studied by phase contrast microscopy (x 2500) and by scanning and transmission electron microscopy. The number of spores and crystals were counted and the size of the protein crystals were determined.

Among the mutants obtained, one (DSM 5480) was selected for its outstanding ability to produce delta-endotoxin.

The amount of delta endotoxin produced by mutant DSM 5480 was compared with that of DSM 2803 the original isolate of *Bacillus thuringiensis subsp. tenebrionis*, *Bacillus thuringiensis subsp. tenebrionis*, strain DSM 5526 used for the production of NOVODOR ®, *Bacillus thuringiensis subsp. tenebrionis*, strain NB178, isolated from Sandoz' *Bacillus thuringiensis tenebrionis* product TRIDENT ® from 1989, strain NB 198, isolated from Sandoz' *B. thuringiensis subsp. tenebrionis* product TRIDENT ® from 1990, "*Bacillus thuringiensis subsp. san diego*", strain NRRL-B-15939, and strain NB 197 isolated from Mycogen's *B. thuringiensis subs. san diego* product M-ONE ® from 1990. As shown in Table I of Example 2 the yield improved mutant of the invention produces 2-3.5 times as much delta endotoxin as the coleopteran active strains of *Bacillus thuringiensis* available today.

EXAMPLE 2

In this example the delta endotoxin yield of *Bacillus thuringiensis subspecies tenebrionis*, mutant DSM 5480 was compared with the delta endotoxin yields of *Bacillus thurinpiensis subspecies tenebrionis* strains DSM 2803 (the original isolate of *Bacillus thuringiensis subsp. tenebrionis*), DSM 5526 (production strain of Novo-Nordisk), and NB 178 and NB 198 (production strains of Sandoz), and *Bacillus thuringiensis subsp. san diego*, strain NRRL-B 15939 and NB 197 (production strains of Mycogen) in a commercial medium. Each of the strains was grown for 17 hours at 30° C. on agar slants of the following composition expressed as gram per litre of distilled water.

| | |
|---|---|
| Peptone, Difco | 5 g |
| Beef extract, Difco | 3 g |
| Agar, Difco | 20 g |
| pH | 7.0 |

5 ml of a suspension of cells from each strain were then transferred to 100 ml of production medium in 500 ml baffle-bottom Erlenmeyer flasks. The production medium consisted of the following components in the quantities indicated (expressed as grams per litre of tap water).

| | |
|---|---|
| Soy bean meal | 50 g |
| Hydrolyzed starch | 40 g |
| $KH_2PO_4$ | 1.77 g |
| $K_2HPO_4$ | 4.53 g |

| | |
|---|---|
| pH | |

The inoculated flasks were incubated at 30.C with shaking (250 rpm). After 96 hours of incubation the culture broths were assayed for delta endotoxin yields by immunological methods.

The amounts of delta endotoxin produced by the individual strains were determined by rocket immuno electrophoresis (RIE) and a photometric immuno assay (PIA) using antibodies raised against purified protein crystals from *Bacillus thuringiensis subsp. tenebrionis*.

400 mg of each culture broth were weighed. 7 ml trisodium phosphate buffer (0.125 M, pH 12) was added to each sample. The suspensions were shaken for 1 hour in order to solubilize the delta endotoxin proteins.

The samples were then centrifuged at 3.500 rpm for 15 minutes and the supernatants were tested for delta-endotoxin by rocket immuno electrophoresis against antiserum raised against purified protein crystals from *B. thuringiensis subsp. tenebrionis*. The amounts of delta endotoxin were determined relatively to a standard with known content of crystal protein.

The concentration of crystal protein was also determined by a photometric immuno assay. The crystal proteins were dissolved in an alkaline solution. The dissolved proteins were precipitated by their antibodies. The rate of this reaction was determined turbidimetrically. The amounts of delta-endotoxin were determined relatively to a standard with known content of crystal protein.

Crystal antigens for production of the antibodies used in the assays were obtained from crystals isolated from *B. thuringiensis subsp. tenebrionis*.

Polyclonal antibodies were raised by injecting rabbits subcutaneously every fortnight with 0.25 mg of crystal antigen.

The results obtained are shown in the following Tables Ia and Ib. Delta endotoxin yields are expressed as BTTU/g (units per g culture broth, determined by rocket immuno electrophoresis, RIE, or by a photometric immuno assay, PIA). The value used for pure *B. thuringiensis subsp. tenebrionis* crystal protein is 500,000 BTTU/g. The values indicated in Table Ia below being averages of 6-7 independent fermentations, and those in Table Ib being averages of 3 independent fermentations.

TABLE Ia

Delta endotoxin production by strains of *Bacillus thuringiensis subsp. tenebrionis* in shakeflasks

| | Delta endotoxin yield | |
|---|---|---|
| Strain | RIE BTTU/g | PIA BTTU/g |
| DSM 2803 | 676 | 1293 |
| NRRL-B 15939 | 747 | 1126 |
| NB 178 | 986 | 1728 |
| DSM 5526 | 1097 | 1860 |
| DSM 5480 | 2382 | 4169 |

TABLE Ib

Delta endotoxin production by strains of *Bacillus thuringiensis subsp. tenebrionis* in shakeflasks

| | Delta endotoxin yield RIE |
|---|---|
| Strain | BTTU/g |
| NB 197 | 1103 |

TABLE Ib-continued

Delta endotoxin production by strains of *Bacillus thuringiensis subsp. tenebrionis* in shakeflasks

| Strain | Delta endotoxin yield RIE BTTU/g |
|---|---|
| NB 198 | 1237 |
| DSM 5480 | 2867 |

From Tables Ia and Ib it appears that DSM 5480 produces more than three times as much delta endotoxin as the original strain of *Bacillus thuringiensis subsp. tenebrionis*, DSM 2803 and "*Bacillus thuringiensis subsp. san diego*", strain NRRL-B15939 and more than twice the amount of delta endotoxin as the strains used today for the manufacture of commercial products of *Bacillus thuringiensis subsp. tenebrionis*.

Phase contrast microscopy, scanning electron microscopy and transmission electron microscopy of *Bacillus thuringiensis subsp. tenebrionis*, mutant DSM 5480 have revealed that the protein crystals produced by this mutant are much bigger than the corresponding protein crystals produced by *Bacillus thuringiensis subsp. tenebrionis*, strains DSM 2803, DSM 5526, NB178 and NB 198, and "*Bacillus thuringiensis subsp. san diego*", strains NRRL-B 15939 and NB 197.

Culture broth of *Bacillus thuringiensis subsp. tenebrionis*, mutant DSM 5480 was tested for activity against colerado potato beetle larvae. The increased amount of delta-endotoxin produced by mutant DSM 5480 as determined by the immunological methods was reflected in the biological activity against colerado potato beetle larvae.

EXAMPLE 3

In this example sporulation and parasporal crystal formation in *B. thuringiensis subsp. tenebrionis*, strains, DSM 2803, DSM 5526, NB 178 and NB 198, and mutant DSM 5480, and "B. thuringiensis subsp. san diego", strains NRRL-B 15939 and NB 197 were compared on solid medium and in liquid medium.

Each of the strains was grown for 2 days at 30° C. on agar plates of the following composition expressed as gram per liter of distilled water.

| Peptone, Difco | 5 g |
|---|---|
| Beef extract, Difco | 3 g |
| Agar, Difco | 20 g |
| pH | 7.0 |

Each of the strains was also grown in liquid medium. All strains were grown for 17 hours at 30° C. on agar slants. 5 ml of a suspension of cells from each strain were then transferred to 500 ml baffle bottom Erlenmeyer flasks each containing 100 ml of medium.

The medium consisted of the following components in the quantities indicated (expressed as grams per liter of tapwater).

| Liquid medium: | |
|---|---|
| Yeast extract | 5 g |
| Tryptone | 5 g |
| Glucose | 1 g |
| KH$_2$PO$_4$ | 0.8 g |
| pH | 7.0 |

The inoculated flasks were incubated at 30° C. with shaking (250 rpm) for 96 hours.

The morphology of the strains on the solid medium and in the liquid medium was studied daily by phase contrast microscopy (x 2500). The number of spores and crystals were counted and the size of the parasporal crystals were determined. A few selected samples were also studied by scanning and transmission electron microscopy.

*B. thuringiensis subsp. tenebrionis*, strains DSM 2803, DSM 5526, NB 178 and NB 198, and "*B. thuringiensis subsp. san diego*", strains NRRL-B 15939 and NB 197 all sporulated well on both media. Before cell lysis each cell contained a spore and a parasporal crystal. The size of the crystals was from 0.4 to 0.9–1.1 μm in length by the time of cell lysis. The average size of the protein crystals being 0.6–0.7 μm in length.

Mutant DSM 5480 produced only few spores ($<10^6$ spores/ml) on the solid medium and in the defined liquid medium. Before cell lysis most cells contained a huge protein crystal but no spore. The size of the protein crystals was from 0.4–0.7 μm to 5.0 μm, the average size of the protein crystals being 2.2–2.3 μm in length.

Ultrastructural analysis of cells from these media by transmission electron microscopy revealed that the sporulation process in the mutant had been started but had not been completed by the time of cell lysis. The sporulation process had reached different stages in the various cells. In cells where the sporulation had only reached stage II (forespore septum formation) the protein crystals filled up the entire cells.

In the production medium (Example 2) the mutant produced a higher number of spores ($10^7$–$10^8$a spores/ml). In this medium the sporulation frequency of the mutant was 10–100 times lower than in the parent strain.

Thus the mutant has retained its ability to produce normal spores. However, the sporulation frequency of the mutuant seems to be strongly dependent of the media.

The size of the protein crystals produced by the individual strains are shown in Tables IIa and IIb.

TABLE IIa

Size of the protein crystals produced by coleopteran active *B. thuringiensis* strains available today.

| | Length of protein crystals in μm | | |
|---|---|---|---|
| Strain | Minimum value | Maximum value | Mean value |
| DSM 2803 | 0.4 | 0.9 | 0.7 |
| NRRL-B-15939 | 0.4 | 0.9 | 0.7 |
| NB 178 | 0.5 | 0.9 | 0.7 |
| DSM 5526 | 0.4 | 0.9 | 0.7 |
| DSM 5480 | 0.7 | 5.0 | 2.3 |

TABLE IIb

Size of the protein crystals produced by coleopteran active *B. thuringiensis* strains available today.

| | Length of protein crystals in μm | | |
|---|---|---|---|
| Strain | Minimum value | Maximum value | Mean value |
| NB 197 | 0.4 | 0.7 | 0.6 |
| NB 198 | 0.4 | 1.1 | 0.7 |
| DSM 5480 | 0.4 | 4.2 | 2.0 |

From Tables IIa and IIb it is clear that mutant DSM 5480 produces much bigger protein crystals than any of the coleopteran active B.t. strains available today.

From the data obtained it appears that the regulation of delta endotoxin production in relation to sporulation has been changed in the mutant.

The mutant seems to produce the protein crystals prior to the development of spores hereby giving the cells a longer period for delta endotoxin production which result in the production of much bigger protein crystals by the time of cell lysis than in the parent strain.

Depending on the available nutrients and the size of the protein crystals in the cells by the time of sporulation a normal spore will be developed before the time of cell lysis.

EXAMPLE 4

In this example the high yielding Btt mutant DSM 5480 was used to produce high potency products for the control of colorado potato beetle larvae.

DSM 5480 was fermented on the production fermentation medium described in example 2 in an aerated, stirred production fermentation tank. After 96 hours, the broth was recovered by centrifugation on a continuous centrifuge.

The concentrated cream which contains the active protein crystals was stabilized by addition of microbial preservatives and pH was adjusted to 5.0.

One portion of the concentrated cream was spray dried and later used for the formulation of wettable powder. The rest of the concentrated cream was used directly for formulation of two aqueous flowable concentrates (FC).

The wettable powder was formulated as described in Table III. The formulation of the two FC's is described in Table IV.

TABLE III

| NOVODOR ® wettable powder formulation | |
|---|---|
| Component | % by weight |
| Spray dried concentrated cream of Btt | 40 |
| Detergents | 9 |
| Anticaking agent | 1 |
| Inert filler | 50 |

TABLE IV

| | NOVODOR ® FC formulations | |
|---|---|---|
| | NOVODOR ® FC 1 | NOVODOR ® FC 2 |
| Component | % by weight | % by weight |
| Btt concentrated cream | 80 | 55 |
| Preservatives | 4 | 4 |
| Antifreeze agents | 9.1 | 19 |
| Detergents | 2.5 | 2.5 |
| pH regulator | 2.85 | 2.85 |
| water | 1.55 | 16.65 |
| | 100.0 | 100.0 |

When using a value of 500,000 BTTU/g of pure crystal protein the content of active crystal protein in the formulations are:

| | | % Btt crystal protein |
|---|---|---|
| NOVODOR ® WP | 70.8 KBTTU/g | 14.16 |
| NOVODOR ® FC1 | 24.7 KBTTU/g | 4.94 |
| NOVODOR ® FC2 | 14.2 KBTTU/g | 2.84 |

The detergents were chosen among the wide selection of suspension aids and wetting agents normally used in agricultural pesticide products.

The anticaking agent is a hydrophilic silica and the inert filler was chosen from the generally used inert fillers such as bentonites, inorganic salts or clays.

The preservates used in the FC's were chosen from the group of food and cosmetic preservatives. The pH regulator is an organic acid.

EXAMPLE 5

A field trial was conducted to prove the biological effect of the high yielding Btt mutant DSM 5480 on the main target pest, colorado potato bettle larvae. In comparison with the two commercial products trident ® and M-one ®. The crop was potatoes.

The crop was sprayed 3 times on Jul. 20th, Jul. 27th and Aug. 3rd (2nd generation larvae). The products and dosages used were:

| | Product volume/acre | Potency KBTTU/g | % Btt crystal protein in the formulation |
|---|---|---|---|
| NOVODOR ® FC 2 | 1 qt/acre | 14.2 | 2.84 |
| | 1.5 qts/acre | 14.2 | 2.84 |
| | 2.5 qts/acre | 14.2 | 2.84 |
| | 3.0 qts/acre | 14.2 | 2.84 |
| TRIDENT ® | 4 qts/acre | 5.5 | 1.10 |
| M-one ® | 2 qts/acre | 8.9 | 1.78 |

The means % control of CPB larvae compared to the untreated control is given in table V. The colorado potato beetle pressure was very heavy in the untreated control: 370 larvae per 20 plants on August 1st and 904 larvae per 20 plants on August 8th.

TABLE V

| | | % control | |
|---|---|---|---|
| Treatment | | August 1st | August 8th |
| NOVODOR ® FC 2 | 1 qt | 99 | 99 |
| NOVODOR ® FC 2 | 1.5 qts | 95 | 100 |
| NOVODOR ® FC 2 | 2.5 qts | 98 | 99 |
| NOVODOR ® FC 2 | 3 qts | 100 | 100 |
| TRIDENT ® | 4 qts | 94 | 98 |
| M-one ® | 2 qts | 98 | 98 |

These results clearly show that products made with the high yielding mutant DSM 5480 are effective for the control of colorado potato beetle larvae in the field. The crystal protein produced by the high yielding strain is fully active as 1.5 qts NOVODOR ® FC give as good results as Trident at 4 qts and as good as M-one at 2 qts.

We claim:

1. A biologically pure culture of *Bacillus thuringiensis* susp. *tenebrionis* having all the identifying characteristics of *Bacillus thuringiensis* susp. tenebrionis, DSM 5480.

* * * * *